US006548069B2

(12) United States Patent
Hymas et al.

(10) Patent No.: US 6,548,069 B2
(45) Date of Patent: Apr. 15, 2003

(54) MULTIVALENT MYCOPLASMA BACTERIN

(75) Inventors: Theo A. Hymas, Valley Center, CA (US); Cynthia L. Becker, Worthington, MN (US)

(73) Assignee: HMV Associates, Inc., Alpine, UT (US)

( * ) Notice: Subject to any disclaimer, the term of this patent is extended or adjusted under 35 U.S.C. 154(b) by 0 days.

(21) Appl. No.: 09/777,008

(22) Filed: Feb. 3, 2001

(65) Prior Publication Data

US 2002/0150593 A1 Oct. 17, 2002

(51) Int. Cl.[7] .................. A61K 39/00; A61K 39/295; A61K 39/02; C12N 1/00
(52) U.S. Cl. .................. 424/201.1; 424/184.1; 424/201.1; 424/202.1; 424/264.1; 435/243
(58) Field of Search .................. 424/201.1, 202.1, 424/184.1, 264.1; 435/243

(56) References Cited

U.S. PATENT DOCUMENTS

| | | | |
|---|---|---|---|
| 5,338,543 A | | 8/1994 | Fitzgerald et al. |
| 5,565,205 A | | 10/1996 | Petersen et al. |
| 5,688,682 A | | 11/1997 | Mulks et al. |
| 5,690,942 A | * | 11/1997 | Hjorth .................. 424/283.1 |
| 5,861,162 A | | 1/1999 | Nagaraja et al. |
| 5,932,705 A | | 8/1999 | Berget et al. |
| 6,015,795 A | | 1/2000 | Hurk et al. |
| 6,083,512 A | * | 7/2000 | Roberts .................. 424/247.1 |
| 6,132,709 A | | 10/2000 | Berg |

OTHER PUBLICATIONS

Howard et al, The Veterinary Record, Oct. 17, 1987.*
Poumarat et al, Veterinary Microbiology, vol. 40, 1994, p. 305–321.*
Tully et al The Mycoplasma—Human and Animal Mycoplasmas, Academic Press Publishers, 1979.*
Confers et al, Am. J. Vet. Res., vol. 48, No. 2, Feb. 1987.*
Rawadi, Methods in Molecular Biology, vol. 104, p. 179–197.*
Al–Aubaidi et al, Cornell Vet., vol. 61, 1971, p. 490–518.*
Cox et al, Vaccine vol. 15, No. 3, 1997, p. 248–256.*
Chanter et al, Can J Vet Res, Apr. 1990, 54, Suppl: S45–47.*
Jasper, Javma, vol. 181, No. 2, Jul. 15, 1982.*
The role of *Mycoplasma* in bovine mastitis, D.E. Jasper, Javma 181:158–162(1982).
Bovine Mycoplasmal Mastitis,D.E. Jasper, Veterinary Medicine Today, 1072–1074.
Mastitis in cows and polyarthritis and pneumonia in claves caused by *Mycoplasma* species bovine group 7, Alexander et al; Australian Veterinary Journal 62:135–136(1985).
Mycoplasma mastitis: An Emerging Disease in Michigan Dairy Cattle, Larry Judge, Michigan Dairy Review 2(2):4(1997).

Molecular Biology and Pathogenicity of Mycoplasmas, Razin et al; Microbiology and Mol. Biology Reviews 62:1094–1156(1998).
Development of a Recombinant Antigen for Antibody –Based Diagnosis of *Mycoplasma bovis* Infection in Cattle, Brank et al; Clinical and Diagnostic Laboratory Immunology 6:861–867(1999).
Mycoplasma Mastitis In Dairy Cattle: If Ignored, It Can Be a Costly Drain On the Milk Producer, Gonzalez online publication http://www.nmconline.org/articles/mycoplasma.htm, 1–7.
Phentypic Switching of Variable Surface Lipoproteins in Mycoplasma bovis Involves High–Frequency Chromosomal Rearrangements, Lysnyansky et al; Journal of Bacteriology 178:5395–5401(1996).
Molecular Cloning and Characterization of an Adherence–Related Operon of *Mycoplasma genitallium*, Reddy et al; Journal of Bacteriology, 5943–5951(1995).
Merck Veterinary Manual, 7th edition, pp. 367–371,1041, 1520,1738.
Development of a Recombinant Antigen for Antibody –Based Diagnosis of *Mycoplasma bovis* Infection in Cattle, Clinical and Diagnostic Laboratory Immunology, Brank et al; 6(6):861–867(1999).
Phenotypic Switching of Variable Surface Lipoproteins in *Mycoplasma bovis* Involves High–Frequency Chromosal Reaarangements, Lysnyansky et al; Journal of Bacteriology 178:5395–5401(1996).
Transgenic plants producing viral and bacterial antigens, Buetow and Korban, AgBiotechNet 2: 1–6(2000).
Erfahrungsbericht zur Anwendung bestandsspezifischer Impfstoffe gegen respiratorische Infektionen mit Beteiligung von Mykoplasma bovis in einem MastrindergroBbestand; Urbaneck et al; Der praktische Tiezarzt 81: 9,756–763 (2000).
Protection against respiratory disease in calves induced by vaccines containing respiratory syncytial virus, parainfluenza type 3 virus, *Mycoplasma bovis* and *M dispar*, Howard et al; Veterinary Record 121: 372–376 (1987).

(List continued on next page.)

*Primary Examiner*—Lynette R. F. Smith
*Assistant Examiner*—Vanessa L. Ford
(74) *Attorney, Agent, or Firm*—Judy Jarecki-Black (57) ABSTRACT

The present invention provides a bacterin comprising at least two virulent *Mycoplasma bovis* isolates of differing biotypes, in an amount sufficient to immunize a calf or cow against infection by *Mycoplasma bovis*, an adjuvant, and a pharmaceutically acceptable carrier. Further provided is a method of producing the bacterin of the present invention. Finally, the present invention also provides a method of immunizing a calf or cow against *Mycoplasma bovis* infection, especially infection associated with BRD, comprising administering to the calf or cow a dose of a bacterin made according to the present invention in an amount effective to elicit a protective response in the animal, as evidenced by a decrease in the mortality and morbidity associated with natural infection.

14 Claims, 1 Drawing Sheet

OTHER PUBLICATIONS

A newly identified immunodominant membrane protein (pMB67) involved in *Mycoplasma bovis* surface antigenic variation, Behrens et al; Microbiology 142:2463–2470 (1996).

Immune Responses to *Mycoplasma bovis* vaccination and Expirimental Infection in the Bovine Mammary Gland, Boothby et al; Can J Vet Res 52: 355–359 (1988).

Vaccines for respiratory disease in cattle, A.R. Peters, Vaccine 5:164 (Sep. 1987).

Immune Response of Cattle to Respiratory Mycoplasmas, Howard et al; Veterinary Immunology and Immunopathology 17:401–412 (1987).

Field trial of a quadrivalent vaccine against calf respiratory disease, Stott et al; The Veterinary Record 121:342–347 (1987).

* cited by examiner

Fig. 1

MULTIVALENT MYCOPLASMA BACTERIN

FIELD OF THE INVENTION

The present invention relates generally to vaccine compositions and methods of making and using the same. More specifically, the invention pertains to a Mycoplasma bacterin demonstrating improved efficacy in protecting cattle from mortality and morbidity associated with Bovine Respiratory Disease complex.

BACKGROUND OF THE INVENTION

Initially called pleuropneumonia-like-organisms (PPLO) because of their similarity to the pleuropneumonia agent of cattle, members of the genus Mycoplasma are opportunistic invaders that cause severe mortality and morbidity in cattle of all ages. Mycoplasma infection has been associated with a variety of bovine diseases including keratoconjunctivitis, mastitis, pneumonia, synovitis, and have been implicated in otitis, abortion and low fertility, and chronic respiratory disease (O'Berry et al, 1966, Jasper, 1982 and Alexander et al, 1985).

The most prevalent and pathogenic species of Mycoplasma isolated from cattle is *M. bovis*, responsible for more than half of the reported isolates in dairy cattle (L. Judge, 1997). Recently, *M. bovis* was identified as a common pathogen in young dairy calves ranging from 14 to approximately 100 days of age. Other strains of Mycoplasma frequently identified as a significant cause of morbidity in cattle include *M. alkalescens* and *M. bovirhinis*.

One of the most important diseases affecting cattle is bovine respiratory disease complex (BRD), which has a huge economic impact worldwide on cattle production. BRD may affect cows and calves but occurs most frequently in younger animals. Although the disease complex involves many different components, including environmental factors, host factors, viruses, bacteria and other infectious agents, Mycoplasma has increasingly been implicated as a cause. Affected cattle show respiratory signs such as fever, depression, anorexia, difficulty breathing, nasal and ocular discharge, coughing, sneezing, gasping, grunting, recumbence and death. Animals may stand with their elbows abducted and their necks extended in an attempt to breath.

Diagnosis of BRD is based on clinical signs with a definitive diagnosis established via culture isolation. However, Mycoplasma can be difficult to culture because its isolation requires reduced oxygen conditions, special culture media, and long culture periods for growth. Complicating treatment of the disease complex is that Mycoplasma are resistant to conventional antibiotic therapy because the organisms lack a cell wall (Razin et al, 1998).

Because no effective antimicrobial therapy exists to treat Mycoplasma infection, prevention relies on instituting effective husbandry measures for control, including providing proper ventilation, reducing the presence of dust and debris, reducing stress, preventing overcrowding, and instituting good animal husbandry procedures including quarantine of new arrivals to prevent the introduction of a Mycoplasma-infected animal into a herd. However, whether quarantine practices will prevent a Mycoplasma-associated outbreak is questionable since the organisms are often found as commensals in the respiratory tract of apparently normal cattle. It has been suggested that Mycoplasma mastitis may result from the transfer of the organism from the lungs to the mammary gland by hematogenous or other routes (Jasper, 1982). Indeed, respiratory outbreaks followed by cases of mastitis that are also antibiotic-resistant have been reported (Gonzalaz, 1992).

*M. bovis* may be asymptomatically present as commensal organisms in the upper respiratory tracts of older animals, where the organisms form a constant source of infection for young animals that are more susceptible to developing clinical disease (Brank et al., 1999). Calves may also be exposed to Mycoplasma infection during calving by contact with the urogenital tract, where Mycoplasma may be shed in the vaginal discharge of heifers. Organisms may also be present in nasal discharges and milk of shedding animals. The prepuce and distal urethra have been found to be colonized by Mycoplasma in the genital tract of apparently normal bulls, resulting in the production of infected semen and may be a path for the dissemination of infection (Jasper et al, 1974).

Vaccination is widely employed as a means to control the morbidity and mortality associated with infectious agents. Generally, vaccines are designed to stimulate a protective immune response in the recipient such that subsequent exposure to the particular infectious agent does not result in disease. Almost all of the vaccines used today to provide immunity against viral or bacterial infections fall into three main categories: 1) live, attenuated organisms, 2) inactivated whole organisms, or 3) subunit vaccines. In all situations, the goal is to present antigens to the recipient's immune system sufficient to produce a protective response without giving the recipient the disease.

Although Mycoplasma infection remains a significant cause of morbidity and mortality for cattle growers, vaccination as a method of preventing Mycoplasma infection is not widely employed. Commercial vaccines with proven efficacy against bovine Mycoplasma species are not readily available and autogenous vaccines have shown little to modest success. Autogenous vaccines are produced from specific samples or isolates of organisms obtained from diseased animals. The products are typically produced by diagnostic laboratories, university diagnostic facilities or commercial suppliers (for example, American Animal Health, Inc., Fort Worth, Tex.). The use of autogenous vaccines to control bovine Mycoplasma infection has been disappointing. Because *M. bovis* exhibits multiple distinct antigens even within a strain, immunization with one strain of Mycoplasma provides little or no cross protection against other strains.

Because of this deficiency and others inherent in the prior art, it would be advantageous to provide a vaccine that induces protection in cattle against Mycoplasma infection, especially one useful in reducing mortality and morbidity associated with BRD.

SUMMARY OF THE INVENTION

Briefly described, the present invention relates to a novel vaccine capable of inducing a protective response in cattle against Mycoplasma infection, especially infection associated with BRD. Further provided is a method of producing the vaccine. Finally, the present invention also provides a method of immunizing a calf or cow against Mycoplasma infection, especially Mycoplasma-associated BRD, comprising administering to the calf or cow a dose of a vaccine made according to the present invention in an amount effective to induce a protective response in the animal.

In one embodiment of the present invention, the vaccine is a whole-cell, inactivated bacterin comprising at least two strains of *Mycoplasma bovis*, an adjuvant and a pharmaceutically acceptable carrier.

In an alternate embodiment, the bacterin of the present invention comprises at least one strain of *Mycoplasma bovis* and, in addition, at least one Mycoplasma isolate of a species other than *M. bovis*. For example, an isolate of *M. alkalescens* or *M. bovirhinis* may be added to the *M. bovis* bacterin.

In yet another embodiment, the present invention provides a synergistic combination vaccine comprising at least one viral, bacterial, fungal or parasitic bovine antigen or antiserum capable of inducing a protective response against a bovine pathogen other than Mycoplasma and, in addition, at least one strain of *Mycoplasma bovis* and at least one strain of a Mycoplasma species other than *M. bovis*. For example, an inactivated or attenuated strain of Pasteurella, Haemophilus or Clostridium may be added to a Mycoplasma bacterin to provide a combination vaccine within the scope of the present invention.

Also provided is a process for the production of a multivalent Mycoplasma bacterin of the present invention. In one embodiment, the vaccine production process comprises culturing at least two Mycoplasma strains; harvesting the cultures; inactivating the cultures to produce a bacterin; adjuvanting the bacterin; and dispensing the bacterin in sterile containers.

The present invention further provides a method for producing a protective immune response in cattle against Mycoplasma infection, especially infection associated with bovine respiratory disease (BRD). In one embodiment, the method for inducing immunity comprises administering to a cow or calf a dose of a Mycoplasma bacterin made according to the present invention in an amount sufficient to protect the animal from BRD.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures, wherein:

FIG. 1 is a graph depicting the results of the vaccine trial conducted under field conditions. Cattle in experimental groups were vaccinated intramuscularly with either a monovalent Mycoplasma vaccine containing one *M. bovis* isolate (group 2), a four component multivalent Mycoplasma vaccine containing three *M. bovis* isolates and one isolate of *M. alkalescens* (group 3) or a 5-component multivalent Mycoplasma vaccine containing three *M. bovis* isolates, one *M. alkalescens* isolate; and one isolate of *M. bovirhinis* (group 4). Controls were unvaccinated for Mycoplasma (group 1). Results of the vaccination trial demonstrate that calves in group 4, vaccinated with the 5-component multivalent Mycoplasma bacterin vaccine, were significantly more protected against mortality associated with BRD than all other groups.

DETAILED DESCRIPTION OF PREFERRED EMBODIMENTS

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents.

For convenience, certain terms employed in the Specification, Examples, and appended claims are collected here.

As used herein, the term "cow" or "cattle" means an animal of bovine origin of any age. Interchangeable terms include "bovine", "calf", "steer", "bull", "heifer" and the like.

As used herein, the term "isolate" means a stock of bacteria obtained from a specific source and maintained in successive cultures or animal inoculations. Isolate is used interchangeably with the term "strain".

As used herein, the term "virulent" means an isolate that retains its ability to be infectious in an animal host.

As used herein, the term "bacterin" means an inactivated bacterial vaccine.

As used herein, the term "inactivated" means a vaccine containing an infectious organism that is no longer capable of replication or growth. Inactivation may be accomplished by a variety of methods including freeze-thawing, chemical treatment (for example, treatment with thimerosal or formalin), sonication, radiation, heat or any other convention means sufficient to prevent replication or growth of the bacteria while maintaining the immunogenicity of the bacterin.

As used herein, the term "immunogenicity" means capable of producing an immune response in a host animal against an antigen or antigens. This immune response forms the basis of the protective immunity elicited by a vaccine against a specific infectious organism.

As used herein, the term "antigen" means a substance that induces a specific immune response in a host animal. An antigen may be introduced into a host or it may be formed within the host.

As used herein, the term "multivalent" means a vaccine containing more than one isolate from the genus Mycoplasma, whether from the same species (i.e., different isolates of *M. bovis*) or from a different Mycoplasma species (i.e., isolates from both *M. bovis* and *M. bovirhinis*). Even for a given genus and species of Mycoplasma, each isolate may share some antigens with other isolates (i.e., "common" antigens), while other antigens will be unique to that isolate. Because a multivalent vaccine provides a greater variety of antigens to the host's immune system, the immune response stimulated in the host is broader than that stimulated by only a single isolate.

As used herein, the term "biotype" means a group of strains or isolates of the same species with common genetic characteristics; that is, members of a particular biotype are genetically identical. One means of classifying members of a species according to biotype is based upon DNA relatedness. DNA relatedness may be determined by a number of conventional methods including, but not limited to, PCR analysis, electrophoresis patterns, fingerprinting methods, and Random Amplified Polymorphic DNA (RAPD) analysis.

As used herein, the term "combination vaccine" means a Mycoplasma bacterin containing at least one other viral, bacterial, fungal or parasitic bovine antigen, antiserum, or antitoxin capable of eliciting a protective response against a cattle pathogen. For example, bovine antigens that provide protection against common cattle pathogens like *Pasteurella multocida*, Salmonella, *Escherichia coli, Haemophilus somnus* and Clostridium sp. are readily available from commercial sources (for example, Omaha Vaccine Co., Omaha, Nev. and Schering-Plough Animal Health, Kenilworth, N.J.) and are suitable for mixing with a Mycoplasma bacterin of the present invention to produce a combination vaccine.

As used herein, the term "adjuvant" means a substance added to a vaccine to increase a vaccine's immunogenicity. The mechanism of how an adjuvant operates is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant), *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-d ioctadecyl-N', N'-bis(2-hydroxyethyl)-propanediamine), paraffin oil, and muramyl dipeptide.

As used herein, the term "pharmaceutically acceptable carrier" means a vehicle for containing the bacterin that can be injected into a bovine host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

The present invention provides a bacterin suitable for administering to a cow or calf to elicit a protective response against BRD and comprising at least two inactivated *Mycoplasma bovis* strains, an adjuvant, and a pharmaceutically acceptable carrier.

In one embodiment of the present invention, a multivalent bacterin is provided comprising at least one strain of *M. bovis* and at least one Mycoplasma isolate of a species other than *M. bovis*. For example, an isolate of *M. alkalescens* or *M. bovirhinis* may be used in addition to at least one strain of *M. bovis*.

Also contemplated to be within the scope of the present invention is a combination vaccine comprising at least one viral, bacterial, fungal or parasitic bovine antigen or antiserum capable of inducing a protective response against a pathogen other than Mycoplasma and, additionally, at least two strains of *Mycoplasma bovis*. Alternately, a combination vaccine of the present invention contains, in addition to at least one viral or bacterial bovine antigen other than Mycoplasma, at least one strain of *Mycoplasma bovis* and at least one strain of a Mycoplasma species other than *M. bovis*. Preferred antigens are those that elicit an immune response that protects a calf or cow from disease but, as will be obvious to one of ordinary skill in the art, antigens useful for combination with the Mycoplasma bacterin will be compatible with each other and with the adjuvant used for Mycoplasma bacterin. As used herein the term "vaccine compatibility" means that each antigen in the combination vaccine does not interfere with the protective response elicited by any other antigen in the vaccine.

Examples of such antigens include, but are not limited to, a protozoan parasitic antigen, a helminth parasite antigen, an ectoparasite antigen, a fungal antigen, a bacterial antigen, a viral antigen and an antiserum. Examples of viral antigens include, but are not limited to, antigens from adenoviruses, caliciviruses, coronaviruses, distemper viruses, hepatitis viruses, herpesviruses, oncogenic viruses, parainfluenza viruses, parvoviruses, rabies viruses, and reoviruses. Examples of bacterial antigens include, but are not limited to, antigens from Actinomyces, Bacillus, Bacteroides, Bordetella, Borrelia, Brucella, Campylobacter, Clostridium, Corynebacterium, Enterococcus, Escherichia, Fusobacterium, Helicobacter, Klebsiella, L-form bacteria, Leptospira, Listeria, Mycobacteria, Neorickettsia, Nocardia, Pasteurella, Peptococcus, Peptostreptococcus, Proteus, Pseudomonas, Rickettsia, Salmonella, Shigella, Staphylococcus, Streptococcus, and Yersinia. Examples of fungal antigens include, but are not limited to, antigens from Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha. Example of protozoan and helminth parasite antigens include, but are not limited to, antigens from Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris, Uncinaria, and Wuchereria. Examples of ectoparasite antigens include, but are not limited to, antigens (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs. Examples of antiserum include, but are not limited to, antibodies against Actiomyces, Pyrogenes, Salmonella, *E. coli*, and *Pasteurella multocida*. One commercial antiserum composition suitable for use in a combination vaccine of the present invention is BO-BAC 2X (Omaha vaccine Co., Omaha, Nev.).

Presently preferred antigens for addition to a Mycoplasma bacterin of the present invention include, but are not limited to, Pasteurella sp., particularly *P. multocida* and *P. haemolytica*, Haemophilus sp., particularly *H. somnus*, and Clostridium sp. In one embodiment of a combination vaccine made according to the present invention, antigens added to the Mycoplasma bacterin are obtained as bovine vaccine strains from a commercial source. Examples of commercial vaccines suitable for use in a combination vaccine according to the present invention include, but are not limited to, ALPHA-7 (Omaha Vaccine Co., Omaha, Nev.); 7-WAY BLACKLEG & PINKEYE (Omaha Vaccine Co., Omaha, Nev.); CATTLEMASTER 4+VL5 (Omaha Vaccine Co., Omaha, Nev.); and autogenous bacterins against *P. haemolytica, P. multocida, H. somnus,* Salmonella, Corynebacterium, Streptococcus, Staphylococcus, Moraxella, *E. coli* and Clostridium (American Animal Health, Inc., Ft. Worth, Tex.).

Mycoplasma strains suitable for use in the present invention may be obtained from a variety of sources. One obvious source is from the inventor. Strains may also be obtained from depositories such as the American Type Culture Collection (ATCC, Manassas, Va.) and National Veterinary Services Laboratories (NVSL, Ames, Iowa). For example, three strains of *M. bovis* and one strain of *M. bovirhinis* are available currently from ATCC.

Because of the widespread dissemination of bovine respiratory disease, numerous virulent strains of *M. bovis, M. alkalescens* or *M. bovirhinis* can also be recovered without undue experimentation by swabbing nasal passages or lung tissue of sick animals and inoculating the material into suitable culture medium. Standard microbiological reference texts, such as "MANUAL OF CLINICAL MICROBIOLOGY," $5^{th}$ edition, ASM Publications, Washington, D.C., 1991, may be consulted to obtain protocols for the isolation and culture of Mycoplasma isolates in a similar fashion.

Because a Mycoplasma isolate may rapidly alter its antigens in culture, high passage strains of greater than about 50 passages may lose infectivity and elicit a poorer immune response when used in a bacterin of the present invention. Therefore, it is preferable to employ freshly isolated strains or cultured strains that are still virulent; that is, strains that have retained the ability to be infectious in the host animal. While no critical number of generations is known to exist, the present invention preferably starts with a Mycoplasma strain which has been passed no more than about ten, and preferably only about five or less times before mass scale production. By using strains with fewer generations in culture, it is believed that the antigens retain their natural state and thus will elicit a protective immune response against the infectious microorganism.

In the present invention, large-scale production is performed with strains of less than ten passages. Strains of five passages are still infectious. The passage number at which a strain loses infectivity and where it ceases to elicit a protective immune response will vary with the strain, but generally occurs somewhere between about 10 and about 50 passages. For the purposes of this application, the term "low-passage" means a strain that remains effective in eliciting an immune response that substantially protects the animal from natural infection or reduces the mortality and morbidity associated with natural infection.

A further aspect of the present invention involves a method for producing a Mycoplasma bacterin that is administered to a cow or calf to elicit a protective response against Mycoplasma infection. Broadly speaking, the method of the present invention comprises the steps of culturing the desired Mycoplasma strains; harvesting the cultures; inactivating the cultures to produce a bacterin; adjuvanting the bacterin; and dispensing the bacterin in sterile containers.

More specifically, the present invention provides a method of producing a bacterin comprising growing at least two virulent isolates of Mycoplasma sp. in culture on a suitable medium; harvesting the Mycoplasma cultures so grown; treating the virulent Mycoplasma harvests with an inactivating agent so as to inactivate the Mycoplasma cultures; concentrating the resulting, inactivated Mycoplasma harvests; recovering the resulting concentrated, inactivated Mycoplasma harvests; adjuvanting the inactivated Mycoplasma and admixing the concentrated, inactivated Mycoplasma harvests so recovered with a suitable physiologically acceptable carrier so as to formulate the bacterin.

The bacterin of the present invention comprises at least two virulent Mycoplasma isolates that display different antigen characteristics, whether from the same species (i.e., different isolates or biotypes of *M. bovis*) or from a different Mycoplasma species (for example, isolates from both *M. bovis* and *M. bovrhinis*). Antigenic variation even among isolates of the same species is readily observed with Mycoplasma. Antigenic variation can be determined using a variety of conventional methods including, but not limited to, differences in culture characteristics; cytotoxicity differences; phenotypic variations; differences in DNA or protein electrophoretic patterns; variations in DNA or RNA fingerprints; and differences in biotype. For example, *M. bovis* isolates useful in the present invention include strains isolated from lung tissue of clinically ill calves and differentiated into at least six different biotypes based upon RAPD analysis.

Mycoplasma strains suitable for use in the present invention comprise either different *M. bovis* biotypes or at least one *M. bovis* isolate and at least one isolate of a species other than *M. bovis*. The virulent isolates of Mycoplasma are grown in culture in a suitable medium. Any culture medium can be used which is suitable for growing Mycoplasma to a concentration sufficient to produce a bacterin that elicits an immune response in a calf or cow against Mycoplasma infection including, but not limited to, a media comprising Mycoplasma broth base, yeast extract, glucose, L-cysteine, ampicillin, thallium acetate, bovine serum and deionized water, prepared as a solid or liquid media. Standard microbiological reference texts are available to allow one of ordinary skill in the art to choose and prepare a culture media to grow Mycoplasma isolates without undue experimentation. For example, the "DIFCO MANUAL," $10^{th}$ edition, Difco Laboratories, Detroit Mich., 1985, and the "MANUAL OF CLINICAL MICROBIOLOGY," $5^{th}$ edition, ASM Publications, Washington, D.C., 1991 (the contents of which are incorporated by reference herein in their entirety), may be consulted to obtain culture protocols. One such medium useful in the present invention to culture Mycoplasma isolates is described in greater detail hereinafter.

The precise conditions under which the isolates are grown may vary depending upon the particular composition of the medium and the specific isolate being grown. The isolate is typically grown from about 48 hours to about 144 hours, measured from the time of incubation to the time of harvest. Once harvested, the amount of Mycoplasma present in the culture can be determined by conventional means including, but not limited to, calculation of colony forming units (CFU), DNA fluorometry (as described in U.S. Pat. No. 5,565,205 to Petersen et al.; the content of which is incorporated herein by reference in its entirety), protein determination, determination of the amount of a Mycoplasma specific antigen (as described in U.S. Pat. No. 5,968,525 to Fitzgerald et al.; the content of which is incorporated herein by reference in its entirety), or changes in cultures parameters like pH. For example, one conventional method used to quantify the amount of protein present in the harvest is the Lowry assay. Alternatively, the amount of Mycoplasma protein can be determined by UV absorption using an appropriate wavelength specific for Mycoplasma. Reference texts such as "METHODS FOR GENERAL AND MOLECULAR BACTERIOLOGY," American Society for Microbiology, Washington, D.C., 1994 (the content of which is incorporated herein by reference in its entirety), can be consulted to obtain protein determination protocols suitable for use by one of ordinary skill in the art to determine Mycoplasma protein content without undue experimentation.

Since the Mycoplasma strains employed in the bacterin of the present invention are infectious, the bacteria are inactivated by adding an inactivating amount of an inactivating agent to the harvest to render it non-infectious. For example, in one embodiment of the present invention, formalin is added to the Mycoplasma harvest to inactivate the culture. As will be appreciated by those of skill in the art, the amount of formalin needed to inactivate the Mycoplasma harvest will depend upon a variety of conditions including, but not limited to, amount of harvest; temperature of inactivation; duration of inactivation period; and concentration of formalin used. For example, one formalin-inactivation protocol suitable for use in the present invention is disclosed by Nakagomi et al in U.S. Pat. No. 6,110,724 (the content of which is incorporated by reference herein in its entirety). Nakagomi et al. teaches formalin-inactivation of a bulk harvest using from about 0.005% (V/V) to about 0.5% (V/V) formalin with an inactivation temperature from about 2 degrees C. to about 38 degrees C. for an inactivation time of about 5 to about 180 days. However, one of skill in the art will recognize that any amount of formalin sufficient to inactivate the Mycoplasma harvest, such that the culture is no longer capable of replication yet continues to maintain immunogenicity such that the inactivated organisms are still capable of eliciting a protective immune response, is suitable for use in the present invention as an inactivating agent. Thus, in one embodiment of the present invention, the Mycoplasma harvest of the present invention is contacted with a 10% formalin solution in a final concentration of about 0.01% v/v to about 0.5% v/v. The culture is then incubated under conditions effective to inactivate the Mycoplasma harvest, e.g., for at least about 12 hours at about 37 degrees C. The harvest may then be centrifuged and washed to remove the excess formalin. In an alternate embodiment, free formaldehyde may be neutralized by adding an equal amount of sodium hydrogen sulfite or can be eliminated by dialysis. Optionally, inactivation may be verified by culturing an aliquot of the inactivated harvest under conditions standard for culturing the Mycoplasma isolate for a time sufficient to determine that the culture is not capable of replication or growth.

While Applicants do not wish to be bound by any particular theory, one reason why formalin inactivation is a suitable means of inactivation may be due to its minimal alteration of the bacterium per se. Formalin is more specific in its action, leaving intact the antigens required to elicit a protective immune response. However, any inactivating agent may be used in the present invention that renders the bacteria incapable of replication while maintaining immunogenicity of the bacterin. Other suitable conventionally-known inactivating agents include, but are not limited to, chemicals like thimerosal (sodium ethyl mercury thiosalicylate or sodium ethyl mercurithio-salicylate), phenol, gluteraldehyde, proteolytic enzymes, beta-propiolactone and binary ethyleneimine.

Thus, in an alternate embodiment of the present invention, the Mycoplasma harvest may be contacted with binary ethyleneimine at a concentration of about 1 mM to about 10 mM, e.g., about 4 mM, as described in U.S. Pat. No. 5,565,205 to Petersen et al., the content of which is incorporated herein by reference in its entirety. Briefly, the Mycoplasma harvest is incubated in the presence of the binary ethyleneimine under conditions effective to inactivate the Mycoplasma harvest, e.g., for at least about 12 hours at about 37 degrees C. The binary ethyleneimine in the culture is then neutralized by adding sodium thiosulfate at an effective neutralizing concentration, e.g., a concentration from about 10 mM to about 20 mM, such as about 16 mM. In one embodiment of the invention, the binary ethyleneimine used to contact and inactivate the Mycoplasma is formed in situ by adding L-bromoethylamine hydrobromide to the culture in an amount which, upon conversion to binary ethyleneimine, results in formation of the desired inactivating concentration, e.g. about 4 mM.

In addition to the use of chemical inactivators, the use of alternate inactivating methods to inactivate the Mycoplasma harvest sufficient to prevent bacterial replication while maintaining immunogenicity of the harvest is contemplated to be within the scope of the present invention. Examples of such methods include, but are not limited to, sonication, radiation, freeze-thawing, detergent lysis, heat treatment and the like.

The inactivating agent is added directly to a Mycoplasma harvest containing one Mycoplasma isolate or comprising a pool of more than one Mycoplasma isolate or, optionally, the Mycoplasma harvest may be washed prior to inactivation to remove residual serum, culture components, and the like.

Additional antigens derived from virulent organisms for use with the Mycoplasma bacterin for a combination vaccine produced according to the present invention may be inactivated by entirely different means than that used to produce the Mycoplasma bacterin however, as will be apparent to one of ordinary skill in the art, the inactivating agents used must be compatible with the inactivating agent used with the Mycoplasma bacterin.

The resulting inactivated Mycoplasma harvest may then be concentrated or diluted to adjust the antigen level to that desired in the final vaccine formulation. Various methods are known in the art for concentrating a bacterial harvest. For example, the organisms may be concentrated by centrifugation, e.g., ultracentrifugation, or by filtration, e.g., ultrafiltration. The concentrated, inactivated Mycoplasma harvest is then recovered, again using methods well known in the art.

The bacterin compositions of the present invention can contain auxiliary substances such as adjuvants; stabilizers like sugars and amino acids; mineral oil; vegetable oil; alum; aluminum phosphate; bentonite; silica; immune enhancers like thymosin and interleukins; polyactic acid; polyglycolic acid; wetting or emulsifying agents; pH buffering agents; gelling or viscosity enhancing additives; preservatives like thimerosal, gentamycin, or mixtures thereof; flavoring agents; colors; and the like, depending upon a variety of factors including, but not limited to the final product desired, the route of administration, and the like.

Another aspect of the present invention involves the addition of an adjuvant to the Mycoplasma bacterin to increase the immunogenicity of the resulting vaccine composition. A number of adjuvants are known in the art which are suitable for increasing the immunogenicity of a bacterin of the present invention including, but not limited to, complete Freund's adjuvant, incomplete Freund's adjuvant, Corynebacterium parvum, Bacillus Calmette Guerin, aluminum hydroxide, glucan, dextran sulfate, DEAE dextran (diethyl amino ethylether dextran), iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-dioctadecyl-N',N'-bis(2-hydroxyethyl)-propanediamine), paraffin oil, muramyl dipeptide and the like. The concentration of the adjuvant may be very broad depending upon a number of factors including the adjuvant used, the route of administration, and the final vaccine composition desired. Standard reference texts, such as VACCINE PROTOCOLS, edited by Robinson et al, Humana Press, Totowa, N.J., 1996, and REMINGTON'S PHARMACEUTICAL SCIENCE, $17^{th}$ edition, 1985 (the contents of which are herein incorporated by reference in their entirety) may be consulted to select a suitable adjuvant and a concentration range without undue experimentation. For example, aluminum hydroxide may be used in the range of up to about 1.5% depending on the route of administration. Concentrations in the range of 0.1 to 1.0% are more typical. Likewise the concentration of DEAE dextran may be broad, e.g., up to about 6% may be used. Oil-in-water adjuvants are typically used in the range of from about 0.01% to about 20%, but more typically is used in concentrations of less than 10%, e.g., from about 0.2 to about 5%.

When the final vaccine comprises different adjuvanted antigens, whether comprising more than one M. bovis biotype; different Mycoplasma species; or different bovine antigens, it is recognized that the change in the concentration of one adjuvant is likely to alter the preferred concentration of the other. Thus, the preferred combination and concentrations of adjuvants used will depend upon a number of considerations, including the antigen components used in the final vaccine and the animal contemplated for vaccination.

Finally, the concentrated, adjuvanted, inactivated Mycoplasma so recovered is admixed with a suitable physiologically acceptable carrier so as to formulate the bacterin. A diluent, dye, or preservatives may also be added. Well known carriers include, but are not limited to, sterile water, saline, or buffered solutions. Additional agents to improve suspendability and dispersion in solution may also be used. A chelator such as EDTA may be added, in an amount for about 0.05% to about 0.20%, particularly at least about 0.07% (w/v) of the bacterin. In an alternate embodiment, an effective concentration of thimerosal, e.g., about 0.005% to about 0.05%, particularly about 0.01% (w/v) may be added as a preservative. It is within the abilities of those skilled in the art to select an appropriate vehicle for the Mycoplasma bacterin depending on the route of administration and condition of the animal to be vaccinated.

Optionally, the bacterin may be rendered isotonic to decrease discomfort associated with administration by injection using any conventional technique, for example, by dialysis against a salt solution that is isotonic with the blood of cattle. Any salt solution suitable for use as an injection medium may be used to render the bacterin isotonic.

The present invention also contemplates treatment or modification of the vaccine harvest depending upon the vaccine delivery method desired. For example, liposome encapsulation, emulsion, microencapsulation, microsphere preparation, the use of polylactic acid and polyglycolic acid, and the like is contemplated to be within the scope of the present invention.

In a similar fashion, the final vaccine harvest may be subjected to freeze-drying or lyophilization using conventional methods to produce a dry formulation. In an alternate embodiment, the vaccine of the present invention may be used in its final state as a liquid by dividing the final harvest into a vial of appropriate volume, for example from about 1 ml to about 50 ml, followed by stopping and sealing the vial.

It will be recognized by one of skill in the art that a bacterin of the present invention may also be produced by any of several modifications of the preceding method. For example, the Mycoplasma harvest may be concentrated before inactivation, rather than after. Also, preparation of the bacterin may be carried out by repeating the inactivation step both before and after the concentrating step. Similarly, the Mycoplasma isolates intended for incorporation into the final vaccine may be pooled after harvest and subsequently processed together to produce the final vaccine or, alternatively, each isolate may be processed individually and pooled in a final step to produce the Mycoplasma bacterin.

The inactivated Mycoplasma bacterin of the present invention may also be used as a component of a vaccine containing one or more other active ingredients, including other bacterial, viral, protozoal or fungal antigens or antitoxins capable of inducing a protective immune response against bovine pathogens, especially those associated with BRD.

A further aspect of the present invention provides a method for administering a Mycoplasma bacterin to a cow or calf in a therapeutically effective amount to elicit a protective immune response against a bovine disease, especially BRD. The dosage will depend on the species, breed, age, size, and health status of the animal to be vaccinated. Other factors like antigen concentration, additional vaccine components, and route of administration (i.e., subcutaneous, intradermal, oral, intramuscular or intravenous administration) will also impact the effective dosage. The route of administration chosen will also depend upon an number of factors including, but not limited to, the animal being vaccinated, vaccination history, the antigens included in the vaccine, and the convenience of the person administering the vaccine.

The dosage of vaccine to administer is easily determinable based on the antigen concentration of the bacterin, the route of administration, and the age and condition of the animal to be vaccinated. Each batch of antigen may be individually calibrated. Alternatively, methodical immunogenicity trials of different dosages, as well as $LD_{50}$ studies and other screening procedures can be used to determine effective dosage for a bacterin of the present invention without undue experimentation. From the examples presented below, it will be readily apparent what approximate dosage would be appropriate. The critical factor is that the dosage provides at least a partial protective effect against natural infection, as evidenced by a reduction in the mortality and morbidity associated with natural infection.

Repeated vaccinations are preferable at periodic time intervals to enhance the immune response initially or after a long period of time since the last dose. In one embodiment of the present invention, the vaccine is administered as a parenteral injection (i.e., subcutaneously, intradermally, or intramuscularly, with intramuscular injection preferred in most cases) in repeated doses of from about one to about five doses, preferably about two to about four injections, and most preferable about two doses, which are given at intervals of about two to about six weeks, preferably from about two to about five weeks. However, one of skill in the art will recognize that the number of doses and the time interval between vaccinations depends on a number of factors including, but not limited to, the age of the animal vaccinated; the condition of the animal; the route of immunization; amount of antigen available per dose; and the like. For initial vaccination, the period will generally be longer than a week and preferably will be between about two to about five weeks. For previously vaccinated animals, a booster vaccination, before or during pregnancy, at about an annual interval may be performed.

The Mycoplasma bacterin may be used alone or in combination with other Bovine antigens for convenience or enhanced results. The combination vaccine preferably provides protection against plural infections. Of particular interest is a combination vaccine comprising a multivalent Mycoplasma bacterin and antigens from other bovine pathogens including, but not limited to, Clostridium sp., Pasteurella sp., particularly *P. multocida* and *P. haemolytica*; and *Haemophilus somnus*, because all cause significant disease in cattle. Additionally, such combinations of antigens do not interfere with each other in their ability to stimulate a protective immune response.

The present invention is further described with respect to the following examples. However, the scope of the invention is not intended to be, and should not be, construed to be limited thereby.

EXAMPLE 1

Isolation of Mycoplasma Strains

Isolates of *Mycoplasma bovis, M. bovirhinis,* and *M. alkalescens* were obtained by culturing samples obtained by swabbing lung tissue of moribund calves diagnosed with BRD. The calves were euthanized and the lungs removed using aseptic conditions. After removal, the cut surface of the lungs was washed with alcohol and sterilized by burning the excess alcohol. Bronchi were opened aseptically and samples taken by swabbing the bronchi and associated areas of the lung. The swabs were used to inoculate Mycoplasma broth or agar plates (Difco PPLO w/o CV, BD Biosciences, Sparks, Md.) and were incubated for approximately 48 hours in 5–10% $CO_2$. In some instances, cultures grown in Mycoplasma broth were subcultured to Mycoplasma plates and incubated for approximately 48 hours in 5–10% $CO_2$. Following culture, Mycoplasma isolates were characterized and identity confirmed using standard microbiological practice.

Select *Mycoplasma bovis* strains were chosen for further characterization by Dr. Ricardo Rosenbusch at the Veterinary Medical Research Institute (Iowa State University, College of Veterinary Medicine, Ames Iowa). Characterization included a determination of cytotoxicity and, in the case of *M. bovis* strains, biotyping according to RAPD analysis. Both cytotoxic ($\geq 40\%$ cytotoxicity) and noncytotoxic strains are pathogenic. Noncytotoxic strains can produce abscesses and be more difficult to control with antibiotics. Upon high passage in culture, all strains become noncytotoxic, while passage in calves accentuates the phenotype as either cytotoxic negative or cytotoxic positive. Using DNA RAPD analysis, *M. bovis* strains isolated as described above were characterized as biotypes II, III, IV, V, or VI. Results of the cytotoxicity testing and RAPD analysis for *M. bovis* Isolates are summarized in the following table:

TABLE 1

Cytotoxicity Testing and RAPD Analysis for *M. bovis* Isolates

| STRAIN | COLONY PICKED | CYTOTOXICITY | DNA RAPD BIOTYPE++ |
|---|---|---|---|
| Lung A | 1# | 0% | IV |
|  | 2 | 86% | Not available |
|  | 3 | 66% | IV |
| Lung B | 1# | 0% | V |
|  | 2 | 33% | V |
|  | 3 | 56% | V |
| Lung E | 1 | 0 | IV |
|  | 2 | 0 | IV |
|  | 3# | 0 | VI |

++Isolates were typed according to band patterns present in DNA gels. There was a clear difference between biotypes, with Biotype VI differing the most from the others.
*M. bovis* isolates chosen as vaccine strains.

EXAMPLE 2

Preparation of Mycoplasma Bacterin

Selected isolates of *M. bovis, M. alkalescens,* and *M. bovirhinis* were cultured in commercial Mycoplasma broth or on Mycoplasma agar plates prepared according to manufacturer's instructions (Difco laboratories, Detroit, Mich.). Isolates chosen for culture included three *M. bovis* isolates (isolate 1 from Lung A, biotype A; Isolate 1 from Lung B, biotype B; and isolate 3 from Lung E, biotype C), one isolate of *M. bovirhinis* and one isolate of *M. alkalescens*. Experimental vaccine serials were prepared as described below and used to vaccinate cattle in an efficacy trial, the results of which are described below in greater detail.

A typical protocol for producing a vaccine according to the present invention is as follows: selected Mycoplasma isolates were inoculated on commercial Mycoplasma agar plates and incubated for 24–48 hours at 35 degrees C. under 5–10% $CO_2$. Colonies were examined to verify morphological characteristics. Typical colonies were inoculated into liquid culture by excising agar around the colony and incubating the excised piece in commercially available Mycoplasma broth. Optionally, identity of colonies can be verified by conventional microbiological means including inhibition of growth in the presence of monospecific antiserum and/or biochemical characterization.

Large scale production of Mycoplasma isolates was performed by growing the isolates in 14 L flasks at about 35 degrees C. for 20 to 100 hours, usually about 48 hours, in liquid culture medium in the presence of about 5–10% $CO_2$. The amount of Mycoplasma present after about 48 hours is determined by conventional means including, but not limited to, removing an aliquot of medium and counting acridine orange-stained cells under a microscope; protein content determination (i.e., by UV absorbance); or by charting pH changes in the culture media (i.e., using an indicator like phenol red to observe a pH decrease in the media). Typical harvests ranged from about $10^6$ CFU/ml to about $10^{10}$ CFU/ml. Once harvested, cultures were then chilled to approximately 4 degrees C., in a refrigerator.

Mycoplasma cultures were inactivated by adding formalin to each flask to a final concentration of approximately 0.2%. Flasks were stirred continuously at 4 degrees C. for at least 24 hours. Culture inactivation can be verified by removing an aliquot of culture, spinning down the cells in a centrifuge, removing the supernatant and washing the pellet with PBS, sterile culture media, or the like to remove excess formalin; culturing an aliquot of the resuspended, washed pellet in liquid media or on an agar plate; and verifying that growth is not present. If necessary to provide for complete inactivation of cultures, additional formalin can be added to harvests; inactivation time or temperature can be increased; or a mixture of the above can be provided to ensure inactivation of Mycoplasma harvest.

Excess formalin can be removed by centrifuging cultures and washing resulting pellets or by dialyzing the inactivated culture, but the concentration of formalin used for inactivation is low enough not to be harmful if not removed.

Experimental harvests were standardized for amount of Mycoplasma present and adjuvanted with a proprietary oil-in-water adjuvant (BioVet Inc., Minn.)

EXAMPLE 3

Mycoplasma Vaccination Trial

Experimental vaccines prepared as described in Example 2 above were tested under field conditions to determine efficacy in reducing mortality and morbidity associated with BRD. Calves were randomly divided into groups and were immunized with either a monovalent vaccine containing only one *M. bovis* isolate or a multivalent vaccine containing three *M. bovis* isolates (one each of biotypes IV, V, and VI) and one *M. alkalescens* isolate. Controls were unvaccinated for Mycoplasma. Results are summarized as follows:

TABLE 2

Vaccination Results

|  | MONO-VALENT[1] | MULTI-VALENT[2] | CONTROLS[3] |
| --- | --- | --- | --- |
| NUMBER OF CALVES PER MONTH | 4,345 | 4,116 | 4,675 |
| MORTALITY (%) | 17.1% | 7.1% | 26.63% |
| DEAD ANIMAL VALUE | $111,750 | $41,020 | $217,875 |
| SICK ANIMALS (TREATED × 1) | 2,235 | 879 | 3734 |
| SICK ANIMALS (TREATED × 2) | 894 | 228 | 1867 |
| SICK ANIMALS (TREATED × 3) | 157 | 44 | 224 |
| TOTAL NO. TREATMENTS | 3286 | 1,151 | 5825 |
| COST OF 1ST TREATMENT | $5,588 | $2,198 | $9343 |
| COST OF 2ND TREATMENT | $2,235 | $570 | $4668 |
| COST OF 3RD TREATMENT | $392 | $110 | $560 |
| TREATED, THEN DIED | 5,588 | 2,198 | 9343 |
| TOTAL MEDICATION COST | $13,803 | $5,076 | $23,914 |
| LABOR COST | $7,560 | $5,670 | $11,340 |
| COST OF SICK AND DEAD CALVES PER MONTH | $133,113 | $51,766 | $253,129 |

MONOVALENT[1]: vaccinated intramuscularly with three doses of a monovalent Mycoplasma vaccine containing only one *M. bovis* isolate;
MULTIVALENT[2]: vaccinated intramuscularly with three doses with a multivalent Mycoplasma vaccine containing three *M. bovis* isolates (one each from biotypes IV, V, and VI) and one strain of *M. alkalescens*;
CONTROLS[3]: unvaccinated for Mycoplasma.

Results showed that vaccination with the monovalent Mycoplasma vaccine provided some protection against mortality and morbidity associated with BRD as compared to unvaccinated controls. However, as seen in Table 2, vaccination with the multivalent Mycoplasma vaccine elicits protection that is significant compared to both the control group and those receiving the monovalent vaccine. The multivalent vaccination protocol resulted in a cost savings of $201,363 as compared to controls and $81,347 compared to calves receiving the monovalent Mycoplasma bacterin.

EXAMPLE 4

Vaccination of Calves with Multivalent Mycoplasma Bacterin

Figure 1:
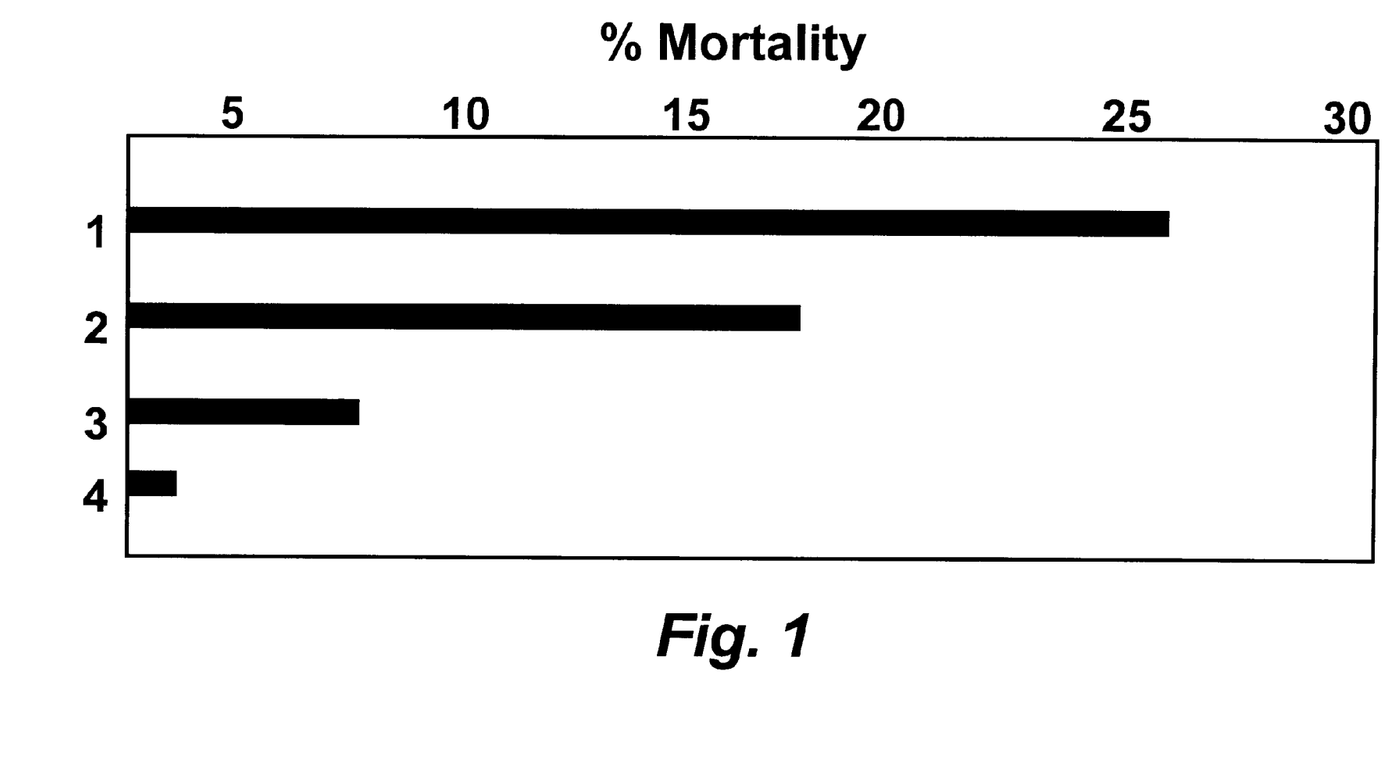

Another vaccination trial was conducted under field conditions using bacterins prepared as described above in Example 2. Calves, 30 to 120 days of age, were vaccinated as described above in Example 3, except that the experimental groups were vaccinated intramuscularly with either a monovalent Mycoplasma vaccine containing one *M. bovis* isolate; a 4-component multivalent Mycoplasma vaccine containing three *M. bovis* isolates and one isolate of *M. alkalescens*; or a 5-component multivalent Mycoplasma vaccine containing three *M. bovis* isolates, one *M. alkalescens* isolate; and one isolate of *M. bovirhinis*. Controls were unvaccinated for Mycoplasma. Referring now to FIG. 1, the graph depicts the results of the vaccination trial and demonstrates that calves vaccinated with the 5-component multivalent Mycoplasma vaccine containing three *M. bovis* isolates, one *M. alkalescens* isolate; and one isolate of *M. bovirhinis* are significantly more protected against mortality associated with BRD than all other groups. Table 3 summarizes the results of the vaccination study, as follows:

TABLE 3

Multivalent Mycoplasma Vaccination Results

| GROUP | NO. OF CALVES (HEAD) | MORTALITY (%) |
| --- | --- | --- |
| MONOVALENT | 17,380 | 17.1% |
| MULTIVALENT[2] | 12,348 | 7.1% |
| MULTIVALENT[3] | 135,833 | 1.3% |
| CONTROLS[4] | 32,725 | 26.6% |

MONOVALENT[1]: vaccinated intramuscularly with three doses of a monovalent Mycoplasma vaccine containing only one *M. bovis* isolate;
MULTIVALENT[2]: vaccinated intramuscularly with three doses with a 4-component multivalent Mycoplasma vaccine containing three *M. bovis* isolates (one each from biotypes IV, V, and VI) and one strain of *M. alkalescens*;
MULTIVALENT[3]: vaccinated intramuscularly with three doses with a 5-component multivalent Mycoplasma vaccine containing three *M. bovis* isolates (one each from biotypes IV, V, and VI), one strain of *M. alkalescens* and one strain of *M. bovirhinis*;
CONTROLS[4]: unvaccinated for Mycoplasma.

As shown in Table 3, all experimental vaccine compositions provide significant protection against BRD, but the most significant protection is seen in the group vaccinated with the 5-component multivalent Mycoplasma vaccine containing three *M. bovis* isolates; one strain of *M. alkalescens*; and one strain of *M. bovirhinis*.

While the invention has been described with reference to specific methods and embodiments, such description is for illustrative purposes only. The words used are words of description rather than of limitation. It is to be understood that changes and variations may be made by those of ordinary skill in the art without departing from the spirit or scope of the present invention, which is set forth in the following claims.

CITED REFERENCES

Alexander, P. G., K. J. Slee, S. McOrist, L. Ireland, and P. J. Coloe. 1985. Mastitis in cows and polyarthritis and pneumonia in calves caused by Mycoplasma species bovine group 7. Aust. Vet. J. 62:135.

Brank, M., D. Le Grand, F. Poumarat, P. Bezille, R. Rosengarten, and C. Citti. 1999. Development if a recombinant antigen for antibody-based diagnosis of *Mycoplasma bovis* infection in cattle. Clin. Diag. Lab. Immun. 6: 861.

Bushnell, R. B. 1984. Mycoplasma mastitis. Vet. Clin. North Am. (Large Anim Pract) 6: 301.

Fraser, G. M., editor. 1991. Mastitis, pp. 686–690 in The Merck Veterinary Manual, 7$^{th}$ edition, Merck & Co., Rahway, N.J.

Gonzalez, R. N. and P. M. Sears. 1994. Diagnosis, control and effect on milk production of *Mycoplasma bovis* intramammary infections. Proc. XVIII World Buiatrics Congress, Bologna, Italy, pp. 681–684.

Gonzalez, R. N., R. A. Merrill, and P. M. Sears. 1992. Shedding of *Mycoplasma bovis* from the udder of naturally infected cows and its importance for diagnosis of bovine intramammary infections. J. Dairy Sci, 75 (Suppl. 1): 259 (Abst.).

Jaspar, D. E. 1979. Bovine mycoplasmal mastitis. J. Am. Vet. Med. Assoc. 175: 1072.

Jasper, D. E. 1982. The role of Mycoplasma in bovine mastitis. J. Amer. Vet. Med. Assoc. 181: 158.

Jasper, D. E., J. M. Al-Aubaidi, and J. Fabricant. 1974. Isolation of Mycoplasma from preputial washings of bulls. Cornell Vet. 64: 296.

Judge, Larry, 1997. Mycoplasma mastitis: an emerging disease in Michigan dairy cattle. *Michigan Dairy Review* 2: 4.

O'Berry, B. A., J. H. Bryner and A. H. Frank, 1966. Isolation of Mycoplasma from an aborted bovine fetus and vaginal mucus. Am. J. Vet. Res. 27: 677.

S. Razin, D. Yogev, and Y. Naot. 1998. Molecular biology and pathogenicity of Mycoplasmas. Microbiol. Mol. Biol. Rev. 62: 1094.

What is claimed is:

1. A vaccine composition comprising
   a) an immunogenically effective amount of (i) at least two killed *Mycoplasma bovis* selected from the group consisting of a biotype IV isolate, a biotype V isolate, a biotype VI isolate, and (ii) a killed *Mycoplasma alkalescens*, wherein said immunogenically effective amount is sufficient to produce a protective response in a vaccinate against Bovine Respiratory Disease resulting from Mycoplasma infection;
   b) an adjuvant; and
   c) a pharmaceutically effective carrier.

2. The vaccine composition of claim 1, further comprising a *Mycoplasma bovirhinis* isolate.

3. The vaccine composition of claim 1, further comprising an immunogenically effective amount of at least one other vaccine against a disease of cattle.

4. The vaccine composition of claim 3, wherein said other vaccine is an antigen selected from a group consisting of a viral antigen, bacterial antigen, fungal antigen, parasitic antigen, and mixtures thereof.

5. The vaccine composition of claim 4, further comprising an immunogenically effective amount of at least one antitoxin against a disease of cattle.

6. The vaccine composition of claim 3, wherein the antigen is a bacterial antigen selected from the group consisting of *Pasteurella multocida, Pasteurella haemolytica*, Clostridium species, *Haemophilus somnus* and combinations thereof.

7. The vaccine composition of claim 1, further comprising an auxiliary agent selected from the group consisting of wetting agents, emulsifying agents, pH buffering agents, gelling additives, viscosity enhancing additives, preservatives, colors and combinations thereof.

8. The vaccine composition of claim 1, wherein the adjuvant is selected from the group consisting of aluminum hydroxide, glucan, dextran sulfate, DEAE dextran (diethyl amino ethylether dextran), oil-in-water, water-in-oil and combinations thereof.

9. The vaccine composition of claim 8, wherein the adjuvant is aluminum hydroxide.

10. The vaccine composition of claim 9, wherein the aluminum hydroxide is present in a final concentration of from about 0.1% to about 20% (w/v).

11. The vaccine composition of claim 9, wherein the aluminum hydroxide is present in a final concentration of about 10% (w/v).

12. The vaccine composition of claim 1, wherein the adjuvant is an oil-in-water adjuvant.

13. The vaccine composition of claim 12, wherein the oil-in-water adjuvant is present in a final concentration from about 0.1% to about 10% (w/v).

14. The vaccine composition of claim 12, wherein the oil-in-water adjuvant is present in a final concentration of about 0.2% to about 5% (w/v).

* * * * *